United States Patent [19]

Moufarrège

[11] Patent Number: 5,591,206
[45] Date of Patent: *Jan. 7, 1997

[54] METHOD AND DEVICE FOR CLOSING WOUNDS

[76] Inventor: Richard Moufarrège, 1111 St. Urbain, Suite M06, Montréal, Québec, Canada, H2Z 1Y6

[*] Notice: The portion of the term of this patent subsequent to Oct. 12, 2014, has been disclaimed.

[21] Appl. No.: 129,309

[22] Filed: Sep. 30, 1993

[51] Int. Cl.$^6$ ................................................. A61B 17/04
[52] U.S. Cl. ..................... 606/215; 606/216; 606/153; 606/154
[58] Field of Search ..................... 606/154, 153, 606/152, 219, 220, 218, 216, 214, 215

[56] References Cited

U.S. PATENT DOCUMENTS

| | | | |
|---|---|---|---|
| 4,766,898 | 8/1988 | Hardy et al. | 606/154 |
| 5,243,973 | 11/1993 | Cook | 606/220 |
| 5,282,829 | 2/1994 | Hermes | 606/220 |

*Primary Examiner*—Gary Jackson

[57] ABSTRACT

A method and a device for holding together a pair of tissue edges defining a wound in a skin layer of a patient, the skin layer having an epidermic top layer and an underlying dermic layer. The device includes a first locking element, a second locking element, a locking structure positioned on either one of the first or second locking element for locking the first locking element to the second locking element. A first grasping structure is positioned on the first locking element for grasping on a portion of the dermic layer positioned adjacent the first locking element. A second grasping structure is positioned on the second locking element for grasping on a portion of the dermic layer positioned adjacent the second locking element. The first and second locking elements are adapted to be inserted by a puncturing action, on each side of the wound, through the epidermic layer and into the dermic layer, so that the first and second locking elements are completely embedded into the dermic layer of the skin. The first and second locking elements are then adapted to be pushed towards one another until the locking structure locks them together adjacent the tissue edges with the first and second grasping structure respectively grasping onto the portion of the dermic layer positioned adjacent the first locking element and the portion of the dermic layer positioned adjacent the second locking element, the first and second locking element thus closing the wound while being embedded into the dermic layer of said skin. The first and second locking elements are made of bioabsorbable material. Since the operation is effected by a puncturing action into the dermic layer, scarring is reduced to a minimum.

10 Claims, 3 Drawing Sheets

METHOD AND DEVICE FOR CLOSING WOUNDS

FIELD OF THE INVENTION

This invention relates to the field of methods and devices for closing wounds and is particularly concerned with a method and a device for minimising the scarring associated with conventional wound closing technology.

BACKGROUND OF THE INVENTION

It is common in the surgical field to close skin wounds by passing a suture through the skin in order to approximate the edges of the skin and hold it stiched in place for healing. Suturing or stiching technics allow the physician to adjust tension, and thus permit approximation on a stich by stich basis. These technics however suffer from various disadvantages. They are labor intensive, time consuming and require manual dexterity on the part of the physician in order to close the wound in such a manner as to minimize scarring. The suturing technics also conventionally require removal of the stiches, thus usually necessitating an additional visit to the physician.

In an effort to reduce the time and labor required for suturing, many medical surgeons have turned to the use of surgical staples. The art of surgical staples is replete with devices and designs of staples and staple appliers. Such devices have now been widely accepted by the medical profession.

While efficient in reducing the time and effort required to close a given wound, the surgical staples suffer from a series of drawbacks. One major disadvantage associated with the use of surgical staples is the formation on the skin of the patient of unesthetical tranversal line marks extending across the suture line. These lines, often referred to as "railway pattern" marks, are mostly imputable to a strangulation by the staples of the connective fibroelastic tissue making up the dermic layer of the skin. Indeed, the swelling of the scarring area causes the elastic fibers of the dermic layer to be pushed against the relatively stiff staples, thus strangeling the fibers.

To minimize this problem, some physicians have resorted to removing the staples after a relatively short period of time. Although helpful in reducing the amount of damage caused to the fibers of the dermic layer, this practice creates a potential risk of dehiscence since the maximal resistance of the wound to tensile stress is only reached after a period of approximately three weeks of recovery.

Another drawback of using suture threads or metal clips on the outside of the skin is that the skin edge portions held together will not be fully accessible for inspection and cleaning, if necessary. They also prevent, at least partially, free "breathing" at the site of the closed incision.

SUMMARY OF THE INVENTION

Accordingly, an object of this invention is to provide an improved method and device for closing wounds.

The improved method of the present invention is based on existing knowledge about the origins of hypertrophic scars and skin scars. It is a well document fact that interruption of the elastic fibers of the dermic layer of the skin causes clearly visible scars. It is also well known that a mere puncturing action with a pointed object does not tear the elastic fibers of the dermic layer. When a pointed object is introduced into the skin by a puncturing movement, the elastic fibers of the dermic layer are merely splited apart in order to allow the passage of the object. Once the object has been removed, the elastic fibers resiliently move back towards one another substantially to their original position. If the object introduced into the skin is removed without tearing the elastic fibers of the dermic layer, there will be practically no scarring of the skin.

The present invention proposes a method of closing wounds which will substantially reduce the risks of tearing or strangulating the elastic fibers of the dermic layer of the skin and which will thus minimize the scarring associated with this type of operation.

The present invention also proposes a method of closing wounds which while minimising the scarring nevertheless allows for a relatively rapid and easy closing of the wound.

The present invention further proposes a device which will allow for realisation of the above mentioned wound closing method.

In accordance with one aspect of the present invention there is provided a device for holding together a pair of tissue edges defining a wound in a skin layer of a patient, said skin layer having an epidermic top layer and an underlying dermic layer, said device being adapted to be puncturingly inserted through both said epidermic top layer and said underlying dermic layer, said device comprising a first substantially elongated locking element; a second substantially elongated locking element; an interlocking means positioned on one of said locking elements for interlocking said first locking element and said second locking element; a first grasping means positioned on said first locking element for grasping on a portion of said dermic layer positioned adjacent said first locking element; a second grasping means positioned on said second locking element for grasping on a portion of said dermic layer positioned adjacent said second locking element; whereby, said first and second locking elements are adapted to be inserted by a puncturing action, on each side of said wound, through said epidermic layer and into said dermic layer, so that said first and second locking elements are embedded into said dermic layer of said skin, and whereby said first and second locking elements are adapted to be pushed towards one another until said locking means locks them together adjacent said tissue edges with said first and second grasping means respectively grasping onto said portion of said dermic layer positioned adjacent said first locking element and said portion of said dermic layer positioned adjacent said second locking element, said first and second locking element thus closing said wound while being embedded into said dermic layer of said skin.

Conveniently, said first locking element has a channel extending longitudinally therethrough, said channel has a channel diameter, said second locking element has a second element cylindrical body, said second element cylindrical body has an external diameter relatively smaller then said channel diameter, whereby said second element cylindrical body is adapted to be at least partially inserted into said channel when said locking means locks said first and second locking elements together.

Preferably, said locking means comprises a plurality of internal peripheral locking rims extending radially and inwardly from said channel of said first locking element, a corresponding plurality of external peripheral locking recesses positioned on the outer periphery of said second element cylindrical body, whereby said locking recesses are adapted to receive said locking rims for locking said first and second locking elements together.

In an alternative embodiment, said locking means comprises a plurality of second element peripheral locking rims extending radially and outwardly from the outer periphery of said second element cylindrical body, a corresponding plurality of first element internal peripheral locking recesses positioned on the inner periphery of said channel of said first locking element, whereby said first element locking recesses are adapted to receive said second element locking rims for locking said first and second locking elements together.

Preferably, said first and second locking elements have a front end and a back end, said first grasping means comprises an external peripheral first grasping flange extending substantially outwardly from said cylindrical body of said first locking element adjacent its back end, and said second grasping means comprises an external peripheral second grasping flange extending substantially outwardly from said cylindrical body of said second locking element adjacent its back end.

Conveniently, said first and second elements have a front end, said first and second grasping flanges each comprise a set of substantially flat trapezium-shaped gripping elements extending respectively from said first and second element cylindrical bodies and said trapezium-shaped elements of said first and second grasping flanges are angled respectively towards said front end of said first and second locking elements.

Preferably, said hollow cylindrical body of said first locking element has a front end and a back end, said back end of said hollow cylindrical body has a substantially annular surface, said front end of said hollow cylindrical body has a substantially angled annular front wall defining a relatively pointed tip.

Also preferably, said second element cylindrical body has a substantially conically tapering front surface merging forwardly into a second element pointed tip.

Conveniently, said first and second locking elements are made of relatively resilient bioabsorbable material.

In accordance with one aspect of the present invention, there is also provided a method for holding together a pair of tissue edges defining a wound in the skin of a patient with a first locking element and a second locking element, said skin having an epidermic layer and a dermic layer, said first locking element having a first grasping means for grasping onto a skin portion adjacent said first locking element and said second locking element having a second grasping means for grasping onto a skin portion adjacent said second locking element, said method comprising the steps of inserting said first and second locking elements by a puncturing action, through said epidermic layer and into said dermic layer of said skin, on each side of said wound so that said first and second locking elements are embedded into said dermic layer; locking said first and second locking elements together on each side of said wound with said first and second grasping means respectively grasping onto said portion of said dermic layer positioned adjacent said first locking element and said portion of said dermic layer positioned adjacent said second locking element, said first and second locking element thus closing said wound while being embedded into said dermic layer of said skin.

BRIEF DESCRIPTION OF THE DRAWINGS

The present invention will be further understood from the following description with reference to the drawings in which.

Similar references are used in different figures to denote similar components.

DETAILED DESCRIPTION

Figure 6:
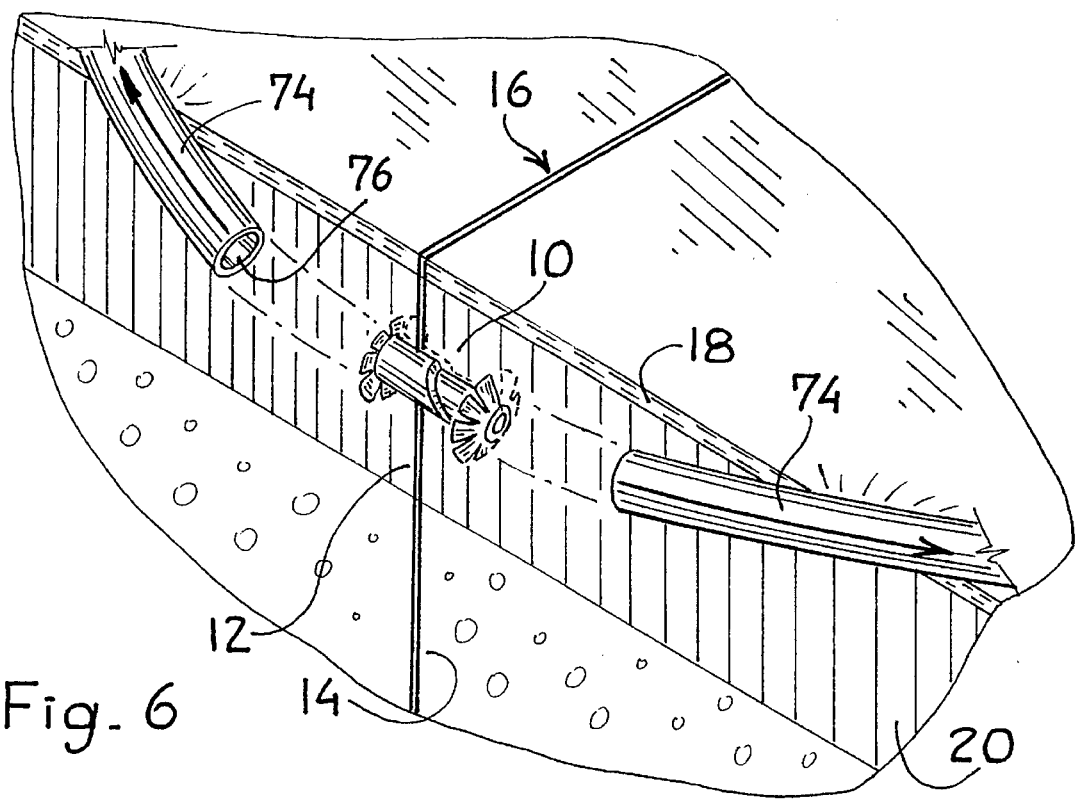
FIG. 6, in a perspective view, illustrates the wound closing device of FIGS. 3 and 4 with its two components in a locked relationship wherein they close the wound.

Referring to FIG. 6, there is shown a wound closing device 10 according to an embodiment of the invention. The wound closing device 10 is shown keeping in apposition a pair of tissue edges 12 and 14 defining a skin incision 16. The reference numeral 18 is used to indicate an epidermic layer while the reference numeral 20 is used to indicate a dermic layer of a skin segment of a patient.

Figure 1:
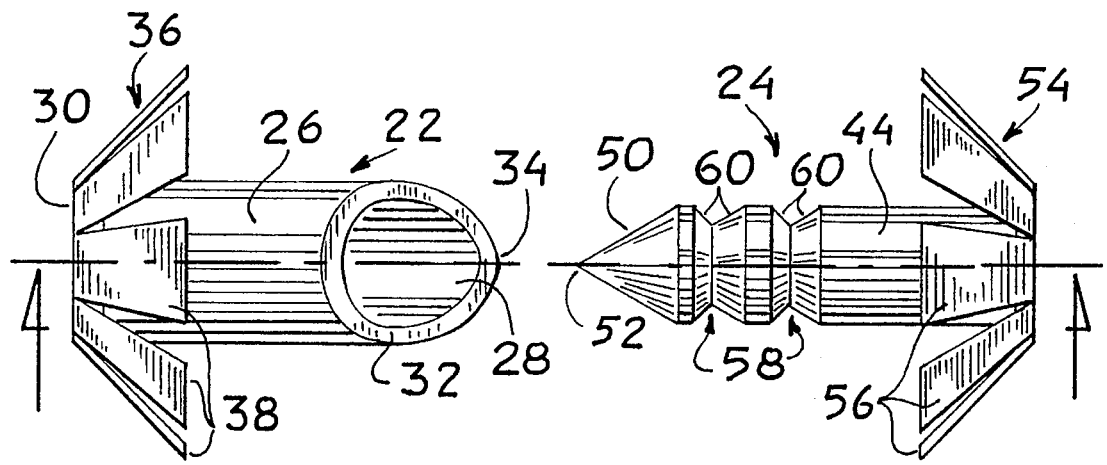
FIG. 1, in a plan view, illustrates a wound closing device in accordance with an embodiment of the present invention.
Figure 2:
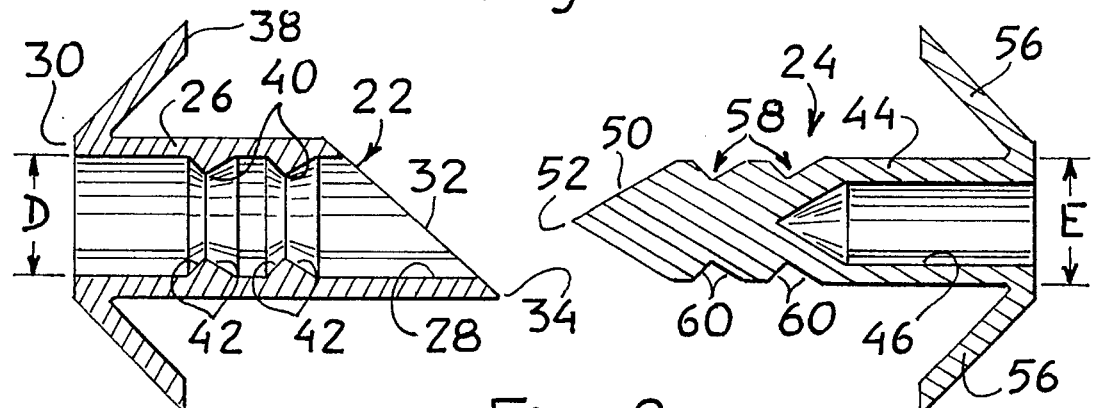
FIG. 2, in a longitudinal cross-sectional view taken along arrow 2—2 of FIG. 1, illustrates the inner configuration of the wound closing device of FIG. 1.

Referring now more specifically to FIG. 1, the wound closing device 10 has a female component 22 and a male component 24. The female component 22 has a hollow cylindrical body 26. The hollow cylindrical body 26 has a channel 28 extending longitudinally therethrough. The internal diameter of the hollow cylindrical body 26 is indicated in FIG. 2 by the reference character D. The cylindrical body 26 has a substantially flat back end defining a substantially annular back wall 28. The front end of the cylindrical body 26 defines a substantially arcuate and angled annular front wall 32. The front wall 32 has a semi-paraboloidic configuration defining a relatively pointed tip 34.

The female component 22 has an external peripheral gripping flange 36 extending integrally from its cylindrical body 26 adjacent its back edge 30. The gripping flange 36 is made up of a set of substantially flat trapezium-shaped gripping elements 38 extending integrally from the cylindrical body 26 and angled towards the front end of the female component 22. The gripping flange 36 is adapted to act as a gripping means for gripping into the dermic layer 20 of the skin.

A set of internal peripheral locking rims 40 extend integrally, radially and inwardly from the channel 28. Each locking rim 40 is defined by a pair of converging angled annular walls 42. The locking rims 40 are adapted to act as locking means for locking the male component 24 and the female component 22 together.

The male component 24 has a substantially cylindrical body 44. The external diameter of the male component 24 is indicated by the reference character E in FIG. 2 and is substantially equal to the internal diameter D of the female component 22. The cylindrical body 44 has a substantially flat back end. A longitudinal channel 46 extends through its back end until about mid-length, thus defining an annular back wall 48 and a rear hollowed out section. The front end of the cylindrical body 44 defines a substantially conically tapering front surface 42 which merges forwardly into a front pointed tip 52.

The male component 24 has an external peripheral gripping flange 54 extending integrally from its cylindrical body 44. The gripping flange 54 is similar to the gripping flange 38 of the female component 22. The gripping flange 54 is made up of a set of substantially flat trapezium-shaped gripping elements 56 extending integrally from the cylindrical body 44 and angled towards the front end of the male component 24. The gripping flange 54 is adapted to act as a gripping means for gripping into the dermic layer 20 of the skin.

A set of external peripheral annular locking recesses 58 are formed integrally on the outer periphery of the cylindrical body 44. Each locking recess 58 is defined by a corresponding pair of substantially angled annular converging walls 60. The locking recesses 58 are adapted to cooperate with the locking rims 40 extending integrally from the cylindrical body 26. The locking recesses 58 and the locking rims 40 are adapted to act as a locking means for locking the male component 24 and the female component 22 together.

Figure 3:
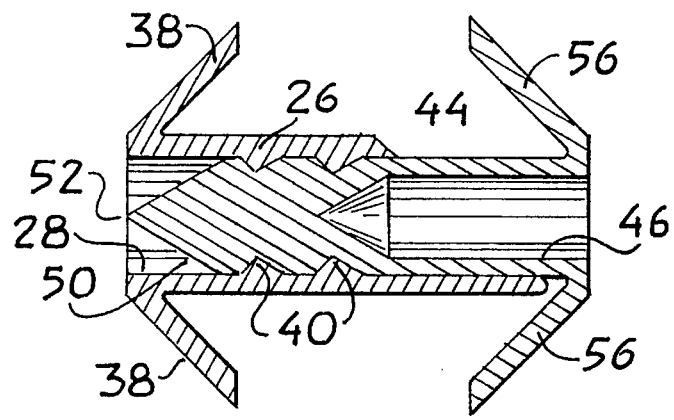
FIG. 3, in a longitudinal cross-sectional view, illustrates the two components of the wound closing device in a locked relationship.

FIG. 3 illustrates, in a longitudinal cross-sectional view, the female component 22 and the male component 24 in a locked relationship. The male component 24 is shown inserted in the channel 28 extending through the body 22. Since the female component 22 and the male component 24 are made of relatively resilient material, they are both adapted to slightly deform under stress, thus allowing the male component 24 to be pushed inside the female component 22 until the locking rims 40 resiliently snap into the corresponding locking recesses 58.

Figure 4:
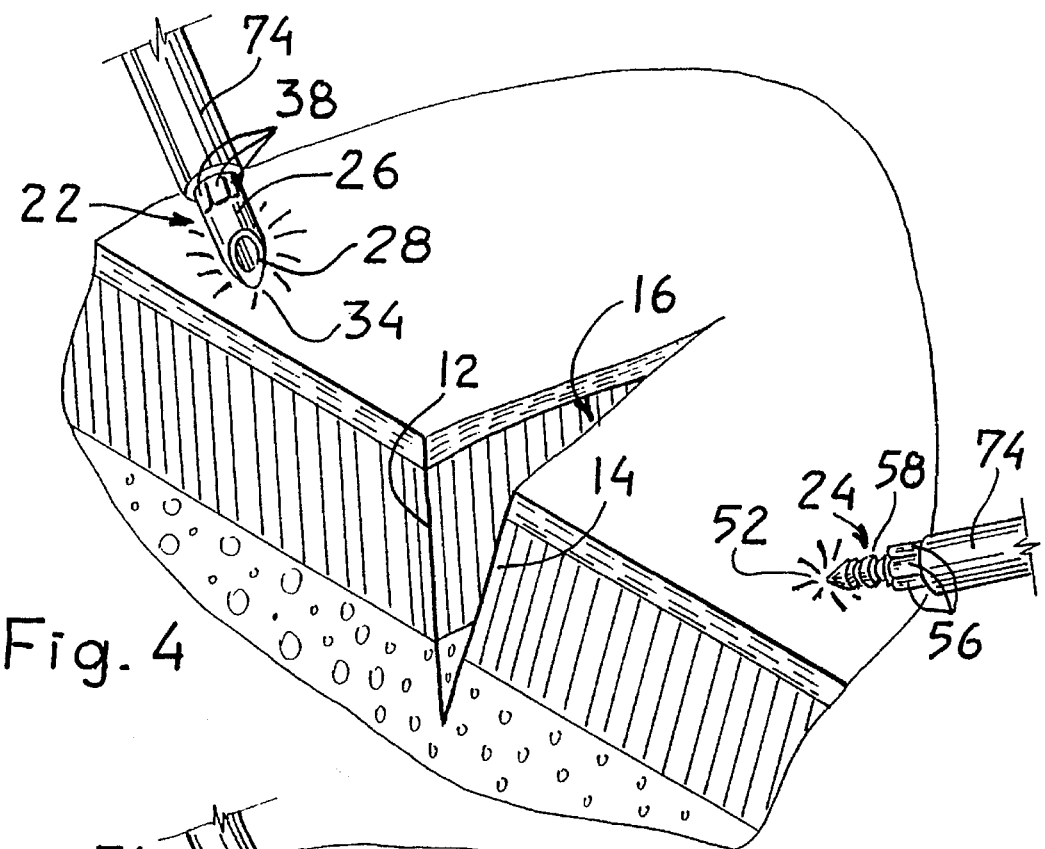
FIG. 4, in a perspective view, illustrates a wound closing device in accordance with an embodiment of the present invention being introduced into the skin of a patient.
Figure 5:
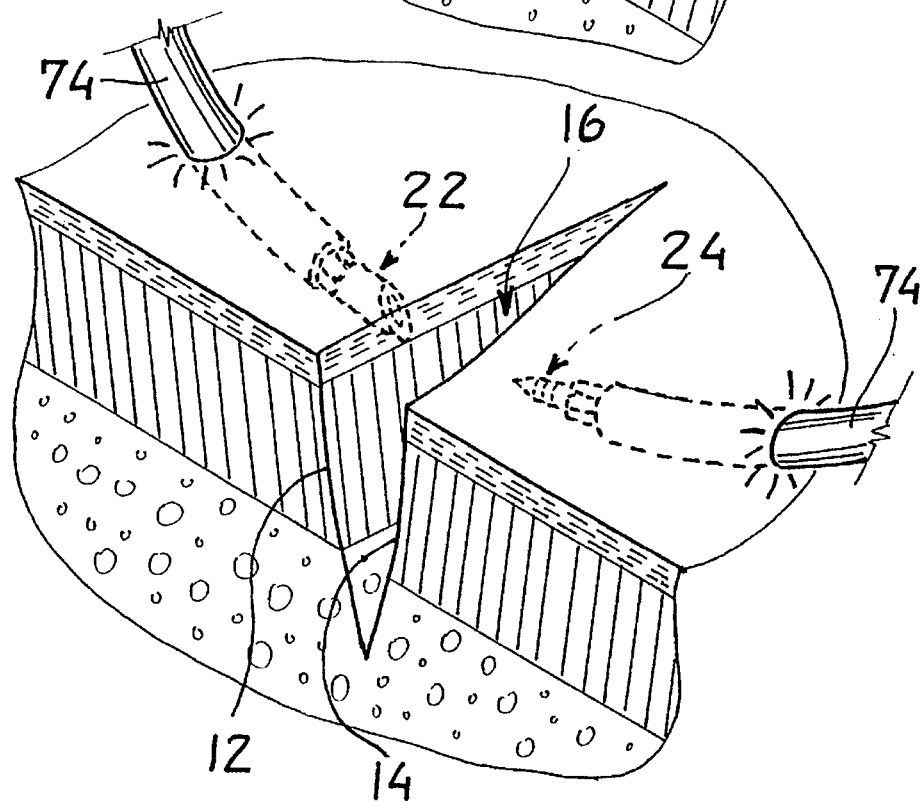
FIG. 5, in a perspective view, illustrates the wound closing device of FIG. 4 being positioned in the dermic layer of the skin, adjacent the edges of a wound.

FIGS. 4, 5 and 6 illustrate a typical sequence during which a wound closing device 10 is used to bring and keep the edges 12 and 14 of the incision 16 into apposition.

Although a schematized inserting tool 62 is depicted in these figures, it should be understood that any suitable inserting tool can be used without departing from the spirit of the invention. The inserting tool 62 illustrated in FIGS. 4 through 7 is schematized in order not to overload the drawings.

The schematized inserting tool 62 has a pair of ferrules 64 extending integrally into a corresponding pair of shank members 66 bended about a pivot pin 68. Each shank member 66 has an upper segment 70 and a lower segment 72. The angle between the upper segment 70 and the lower segment 72 is designated by the reference character C in FIG. 7. The angle C is typically approximately 120 degrees. Each lower segment 72 extends integrally into a hollow cylindrical retaining arm 74. Each retaining arm 74 has a substantially parabolically shaped configuration and a correspondingly shaped channel 76 extending therethrough. The upper segments 70 of the shank members 66 are biased apart by a leaf-type spring 78.

As can be seen more specifically in FIGS. 4 and 5, the female component 22 and the male component 24 are each adapted to be partially inserted into a facing pair of channels 76. When the rear end of the components 22 and 24 is slidably inserted in a channel 76, each one of the gripping elements 38 and 56 respectively making up the gripping flanges 36 and 54, is adapted to bended forwardly about its integral connection with the respective cylindrical bodies 26 and 44. When the gripping elements 38 and 56 are in their bended configuration they are adapted to lie substantially flat against the respective cylindrical bodies 22 and 24. The trapezium configuration of the gripping elements 38 and 56 allows them to be bended without overlapping one on top of the other.

Figure 7:
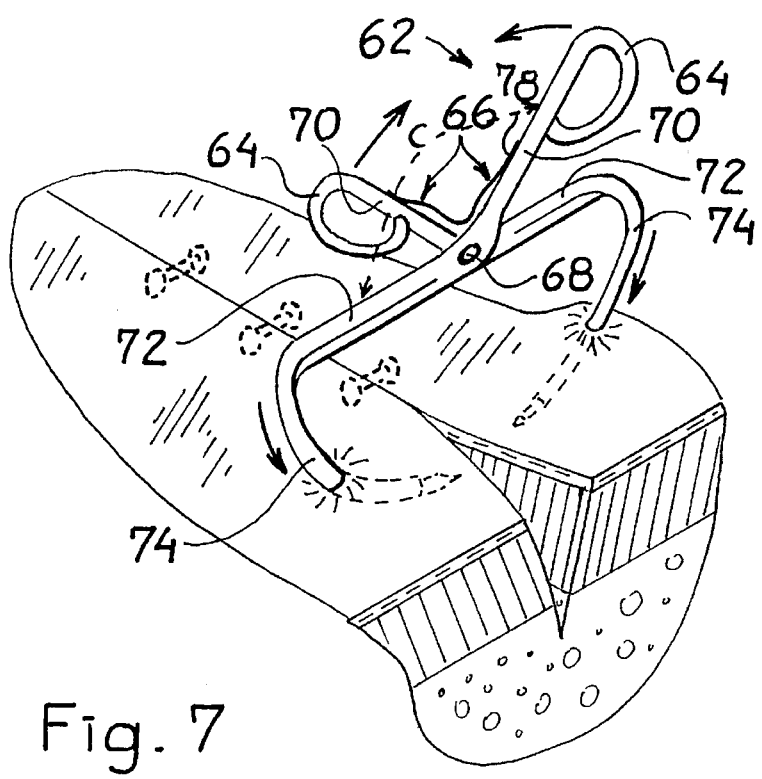
FIG. 7, in a perspective view illustrates a wound being closed by the wound closing method of the present invention, using a set of wound closing devices in accordance with an embodiment of the invention.

Once the rear end of the components 22 and 24 has been inserted in a channel 76, it is frictionally and releasably secured to a corresponding retaining arm 74. In use, once the rear end of the components 22 and 24 has been inserted in a substantially facing pair of channels 76, the tool 62 is manipulated by the physician until the tips 34 and 52 are put in contact with the upper surface of the dermic layer 18 on each side of the incision 16 as illustrated in FIG. 4. With is fingers inserted in the ferrules 64, the physician then squeezes the latter towards each other thus pivoting the shanks 66 about the pivot pin 68 and correspondingly pivoting the retaining arms 74 towards one another. The shanks 66 and the retaining arms 74 are configured and sized so that by pivoting the retaining arms 74 towards one another, the physician forces the elements 22 and 24 through the epidermic layer 18 and into the dermic layer 20 as illustrated in FIGS. 5 and 7. The parabolically shaped configuration of the retaining arms 74 allows the components 22 and 24 to travel through the epidermic and dermic layers 18 and 20 in a corresponding parabolical pattern bringing them in apposition at the suturing site. The male component 24 and the female component 22 are thus introduced and pushed through the epidermic layer 18 and the dermic layer 20 by a curved puncturing movement resulting from a mere squeezing action on the ferrules 64 of the tool 62.

The displacement of the components 22 and 24 through the dermic layer 20 combined with the movement of the retaining arms 74 causes the tissue edges 12 and 14 to move toward one another in order to close the wound 16. In some instances, the physician may assist or initiate this joining movement of the tissue edges 12 and 14 by a pinching action or any other suitable method.

Once the components 22 and 24 have been brought into contact with each other on each side of the closed incision 16, the physician continues to squeeze the ferrules 64 so that the male component 24 is pushed inside the female component 22 until the locking rims 40 resiliently snap into the corresponding locking recesses 58, thus locking the components 22 and 24 together.

The components 22 and 24 being locked together the physician then release is squeezing action on the ferrules 64 and the spring 78 biases the upper segments 70 of the shank members 66 apart. As illustrated more specifically in FIG. 6, when the retaining arms 74 are moved away from each other while the components 22 and 24 are in a locked relationship, the gripping elements 38 and 56 respectively making up the gripping flanges 36 and 54 slide out of the channels 76. When the gripping flanges 36 and 54 which were frictionally held inside the channels 76 are removed from the latter, the gripping elements 38 and 56 resiliently spring back to their original unfolded configuration illustrated in FIGS. 1, 2, 3 and 6. In this unfolded position, the gripping flanges 36 and 54 act as a gripping means for gripping into the dermic layer 20 and preventing the separation of the tissue edges 12 and 14.

The retaining arms 74 are then fully retracted from both the dermic and epidermic layers 20 and 18, and the operation is repeated if necessary at another location on the incision 16.

As mentioned previously, it is well known in the medical field that substantially visible scarring of the skin only occurs when the elastic fibers of the dermic layer are interrupted. The insertion of the male and female components 24 and 22 of the present invention through the dermic layer 20 being the effect of a puncturing action, the suturing process of the present invention thus only temporarily spaces apart the elastic fibers and thus minimizes the associated scarring.

In a preferred embodiment of the invention, the female component 24 and the male component 22 are injection molded out of a bioabsorbable material such as a polyglycolic acid polymer. The components 22 and 24 are thus left inside the dermic layer without the need for a time consuming and scar creating suture removal operation.

Numerous modifications, variations and adaptations may be made to the particular embodiments of the invention described above without departing from the scope of the invention, which is defined in the claims.

The embodiments of the invention in which an exclusive property or privilege is claimed are defined as follows:

1. A device for holding together a pair of tissue edges defining a wound in a skin layer of a patient, said skin layer having an epidermic top layer and an underlying dermic layer, said device being adapted to be puncturingly inserted through both said epidermic top layer and said underlying dermic layer said device comprising:

a first substantially elongated locking element;

a second substantially elongated locking element;

an interlocking means positioned on one of said locking elements for interlocking said first locking element and said second locking element;

a first grasping means positioned on said first locking element for grasping on a portion of said dermic layer positioned adjacent said first locking element;

a second grasping means positioned on said second locking element for grasping on a portion of said dermic layer positioned adjacent said second locking element;

whereby, said first and second locking elements are adapted to be inserted by a puncturing action, on each side of said wound, through said epidermic layer and into said dermic layer, so that said first and second locking elements are embedded into said dermic layer of said skin, and whereby said first and second locking elements are adapted to be pushed towards one another until said locking means locks them together adjacent said tissue edges with said first and second grasping means respectively grasping onto said portion of said dermic layer positioned adjacent said first locking element and said portion of said dermic layer positioned adjacent said second locking element, said first and second locking element thus closing said wound while being embedded into said dermic layer of said skin.

2. A device as recited in claim 1 wherein, said first locking element has a channel extending longitudinally therethrough, said channel has a channel diameter, said second locking element has a second element cylindrical body, said second element cylindrical body has an external diameter smaller then said channel diameter, whereby said second element cylindrical body is adapted to be at least partially inserted into said channel when said locking means locks said first and second locking elements together.

3. A device as recited in claim 2 wherein said locking means comprises a plurality of internal peripheral locking rims extending radially and inwardly from said channel of said first locking element, a corresponding plurality of external peripheral locking recesses positioned on the outer periphery of said second element cylindrical body, whereby said locking recesses are adapted to receive said locking rims for locking said first and second locking elements together.

4. A device as recited in claim 2 wherein said locking means comprises a plurality of second element peripheral locking rims extending radially and outwardly from the outer periphery of said second element cylindrical body, a corresponding plurality of first element internal peripheral locking recesses positioned on the inner periphery of said channel of said first locking element, whereby said first elementlocking recesses are adapted to receive said second element locking rims for locking said first and second locking elements together.

5. A device as recited in claim 2 wherein said first and second locking elements have a front end and a back end, said first grasping means comprises an external peripheral first grasping flange extending substantially outwardly from said cylindrical body of said first locking element adjacent its back end, and said second grasping means comprises an external peripheral second grasping flange extending substantially outwardly from said cylindrical body of said second locking element adjacent its back end.

6. A device as recited in claim 5 wherein said first and second elements have a front end, said first and second grasping flanges each comprise a set of substantially flat trapezium-shaped gripping elements extending respectively from said first and second element cylindrical bodies and said trapezium-shaped elements of said first and second grasping flanges are angled respectively towards said front end of said first and second locking elements.

7. A device as recited in claim 2 wherein said hollow cylindrical body of said first locking element has a front end and a back end, said back end of said hollow cylindrical body has a substantially annular surface, said front end of said hollow cylindrical body has a substantially angled annular front wall defining a relatively pointed tip.

8. A device as recited in claim 2 wherein said second element cylindrical body has a substantially conically tapering front surface merging forwardly into a second element pointed tip.

9. A device as recited in claim 1 wherein said first and second locking elements are made of relatively resilient bioabsorbable material.

10. A method for holding together a pair of tissue edges defining a wound in the skin of a patient with a first locking element and a second locking element, said skin having an epidermic layer and a dermic layer, said first locking element having a first grasping means for grasping onto a skin portion adjacent said first locking element and said second locking element having a second grasping means for grasping onto a skin portion adjacent said second locking element, said method comprising the steps of:

inserting said first and second locking elements by a puncturing action, through said epidermic layer and into said dermic layer of said skin, on each side of said wound so that said first and second locking elements are embedded into said dermic layer;

locking said first and second locking elements together on each side of said wound with said first and second grasping means respectively grasping onto said portion of said dermic layer positioned adjacent said first locking element and said portion of said dermic layer positioned adjacent said second locking element, said first and second locking element thus closing said wound while being embedded into said dermic layer of said skin.

* * * * *